United States Patent
Suzuki (10) Patent No.: US 8,578,756 B2
(45) Date of Patent: Nov. 12, 2013

(54) PARTICULATE MATTER DETECTION SENSOR AND PARTICULATE MATTER DETECTION SENSOR UNIT

(75) Inventor: Toshiyuki Suzuki, Kiyosu (JP)

(73) Assignee: Denso Corporation, Kariya (JP)

(*) Notice: Subject to any disclaimer, the term of this patent is extended or adjusted under 35 U.S.C. 154(b) by 246 days.

(21) Appl. No.: 13/114,318

(22) Filed: May 24, 2011

(65) Prior Publication Data

US 2011/0283773 A1    Nov. 24, 2011

(30) Foreign Application Priority Data

May 24, 2010  (JP) ................. 2010-118837

(51) Int. Cl.
 *G01N 15/06* (2006.01)
 *G01N 31/00* (2006.01)
(52) U.S. Cl.
 USPC ........ 73/28.01; 73/23.31; 73/23.33; 73/25.05
(58) Field of Classification Search
 USPC .............. 73/23.31–23.33, 25.01–25.05, 73/28.01–28.06
 See application file for complete search history.

(56) References Cited

U.S. PATENT DOCUMENTS

| | | | | |
|---|---|---|---|---|
| 6,634,210 | B1* | 10/2003 | Bosch et al. | 73/23.33 |
| 7,543,477 | B2* | 6/2009 | Berger et al. | 73/23.33 |
| 7,644,609 | B2* | 1/2010 | Reutiman et al. | 73/114.69 |
| 7,770,432 | B2* | 8/2010 | Roesch et al. | 73/23.33 |
| 8,151,626 | B2* | 4/2012 | Krafthefer et al. | 73/28.01 |
| 8,176,768 | B2* | 5/2012 | Kondo et al. | 73/23.33 |
| 8,182,665 | B2* | 5/2012 | Dorfmueller et al. | 204/426 |
| 8,225,640 | B2* | 7/2012 | Nelson et al. | 73/28.01 |
| 8,230,716 | B2* | 7/2012 | Nelson et al. | 73/1.06 |
| 8,249,827 | B2* | 8/2012 | Nelson et al. | 702/183 |
| 8,382,884 | B2* | 2/2013 | Okayama et al. | 96/19 |
| 2008/0264146 | A1* | 10/2008 | Roesch et al. | 73/23.33 |
| 2009/0217737 | A1* | 9/2009 | Dorfmueller et al. | 73/28.01 |
| 2010/0107737 | A1* | 5/2010 | Krafthefer et al. | 73/28.01 |
| 2010/0180668 | A1* | 7/2010 | Kruse et al. | 73/28.01 |
| 2011/0030451 | A1* | 2/2011 | Roesch et al. | 73/28.02 |

(Continued)

FOREIGN PATENT DOCUMENTS

JP    60-1546    1/1985

OTHER PUBLICATIONS

Ballou, Glen, ed. Handbook for Sound Engineers, p. 214. Elsevier, Inc. 2002.*

*Primary Examiner* — Leonard Chang
*Assistant Examiner* — Natalie Huls
(74) *Attorney, Agent, or Firm* — Nixon & Vanderhye PC (57) ABSTRACT

In a PM detection sensor with a sensor element having a pair of detection electrodes formed on a substrate, quantity of PM accumulated in the detection electrode is calculated on the basis of a resistance change between the detection electrodes. A series circuit composed of a temperature detection resistance and a capacitor connected in series is formed on a conductive path in the sensor element. A microcomputer in an ECU instructs a power source to supply a DC voltage to the resistance and the capacitor to make a first state in which no current flows in the resistance when a quantity of PM accumulated in the sensor element is detected. The microcomputer instructs the power source to supply an AC voltage to the resistance and the capacitor to make a second state in which a current flows in the resistance when a temperature of the sensor element is detected.

11 Claims, 5 Drawing Sheets

(56) References Cited

U.S. PATENT DOCUMENTS

| | | | |
|---|---|---|---|
| 2011/0156727 A1* | 6/2011 | Achhammer et al. | 324/691 |
| 2011/0209523 A1* | 9/2011 | Otsubo et al. | 73/23.31 |
| 2011/0252865 A1* | 10/2011 | Tokuda et al. | 73/23.31 |
| 2011/0259079 A1* | 10/2011 | Maeda et al. | 73/23.33 |
| 2011/0314899 A1* | 12/2011 | Di Miro et al. | 73/23.33 |
| 2012/0103059 A1* | 5/2012 | Kimata et al. | 73/23.33 |
| 2012/0119759 A1* | 5/2012 | Nelson et al. | 324/691 |
| 2012/0120981 A1* | 5/2012 | Genssle et al. | 374/1 |
| 2012/0247181 A1* | 10/2012 | Nishijima | 73/23.33 |
| 2012/0291632 A1* | 11/2012 | Nishijima | 96/421 |
| 2012/0324982 A1* | 12/2012 | Hocken et al. | 73/28.01 |

* cited by examiner

PARTICULATE MATTER DETECTION SENSOR AND PARTICULATE MATTER DETECTION SENSOR UNIT

CROSS-REFERENCE TO RELATED APPLICATION

This application is related to and claims priority from Japanese Patent Application No. 2010-118837 filed on May 24, 2010, the contents of which are hereby incorporated by reference.

BACKGROUND OF THE INVENTION

1. Field of the Invention

The present invention relates to particulate matter detection sensors and particulate matter detection sensor units capable of detecting a quantity of particulate matter contained in target detection gas such as exhaust gas emitted from an internal combustion engine.

2. Description of the Related Art

In general, a diesel engine exhaust gas system is equipped with a diesel particulate filter (DPF). Such a DPF can eliminate conductive particulate matter PM from exhaust gas emitted from a diesel engine. That is, the DPF captures particulate matter PM contained in exhaust gas. The particulate matter PM captured in the DPF is oxidized at a high temperature of the exhaust gas. In other words, the DPF is regenerated at a high temperature. In order to execute the DPF regeneration process, it is necessary to calculate the quantity of particulate matter PM captured by the DPF. The DPF regeneration process is executed at the timing when the calculated quantity of particulate matter PM in the DPF exceeds a predetermined value.

There have been proposed various conventional methods of calculating the quantity of particulate matter PM captured in a DPF. One of the conventional methods uses a particulate matter PM detection sensor (or the PM detection sensor or smoke sensor for short) capable of detecting a quantity of particulate matter contained in exhaust gas. The detected quantity of particulate matter contained in such exhaust gas corresponds to the quantity of particulate matter accumulated in the DPF and the period of using the DPF. For example, Japanese patent laid open publication No. JP S60-1546 discloses such a PM detection sensor. In the conventional technique disclosed in Japanese patent laid open publication No. JP S60-1546, a pair of detection electrodes is formed on a substrate. The detection electrodes have a comb structure and face to each other on the substrate. The detection electrodes are electrically connected to detection terminals, respectively. The quantity of particulate matter PM contained in exhaust gas can be detected on the basis of a resistance change between the detection electrodes in the PM detection sensor. The resistance change occurs on the basis of the quantity of particulate matter PM accumulated between the detection electrodes.

In the PM detection sensor disclosed in Japanese patent laid open publication No. JP S60-4546, a pair of temperature adjusting electrodes is further formed on a front surface and a back surface of the substrate in addition to the detection electrodes. The temperature adjusting electrodes are electrically connected to a temperature adjusting terminal. This structure of the PM detection sensor makes it possible to correctly detect the concentration of particulate matter PM contained in exhaust gas without influence of the temperature dependence of the resistance between the detection electrodes.

Such a PM detection sensor is further applied to fault diagnosis of a DPF other than applied to the process of calculating the quantity of particulate matter PM accumulated in the DPF. That is, when a DPF failure occurs, exhaust gas containing an excess amount of particulate matter PM flows at the downstream of the DPF in the exhaust gas purifying system. In order to detect the occurrence of DPF failure, the PM detection sensor is placed at the downstream side of the DPF. The fault diagnosis is executed on the basis of the quantity of particulate matter PM contained in the exhaust gas at the downstream side of the DPF.

However, because being equipped with the temperature adjusting electrodes, the conventional particulate matter detection sensors, for example, disclosed in Japanese patent laid open publication No. JP S60-1546, suppress the influence of the temperature dependence of the detected resistance when the quantity of particulate matter PM contained in exhaust gas is detected, and therefore cannot detect the temperature of exhaust gas.

Further, the conventional PM detection sensor previously described has wires to be used for detecting the quantity of particulate matter PM and wires to be connected to the temperature adjusting electrodes. This causes a complicated circuit configuration and increased number of terminals.

Still further, in order to have the function of detecting the temperature of exhaust gas, it is necessary to have additional wires and terminals in the conventional particulate matter detection sensor. This increases the conventional problem previously described.

SUMMARY OF THE INVENTION

It is an object of the present invention to provide a particulate matter detection sensor and a particulate matter detection sensor unit equipped with the particulate matter detection sensor with a simple structure capable of detecting a quantity of conductive particulate matter PM contained in exhaust gas and detecting a temperature of the exhaust gas. Further, the present invention provides a particulate matter detection sensor system comprised of a control device and the particulate matter detection sensor unit capable of receiving the detection signals transferred from the particulate matter detection sensor, and calculating the quantity of conductive particulate matter PM accumulated in the sensor element and the temperature of the sensor element in the particulate matter detection sensor on the basis of the received detection signals.

To achieve the above purposes, the present invention provides a particulate matter detection sensor as one aspect of the present invention. The particulate matter detection sensor is comprises of a sensor element. The sensor element is capable of detecting particulate matter of conductive characteristics contained in a target detection gas such as exhaust gas emitted from an internal combustion engine. The sensor element is comprised of a substrate, a pair of detection electrodes, a temperature detection resistance, and a switching means. The pair of detection electrodes is formed on the substrate. The detection electrodes face to each other. The temperature detection resistance is formed in a conductive path between the pair of the detection electrodes. The temperature of the sensor element is detected on the basis of a resistance value of the temperature detection resistance. The switching means making a first state and second state. In the first state, no current flows through the temperature detection resistance and a quantity of particulate matter accumulated in the sensor element is detected. In the second state, the current flows through the temperature detection resistance and a temperature of the sensor element is detected. A quantity of particulate matter accumulated between the detection electrodes is detected on the basis of a change of the resistance value between the detection electrodes caused by the accumulated particulate matters of conductive characteristics.

In accordance with another aspect of the present invention, there is provided a particulate matter detection sensor unit comprised of the sensor element and a sensor connector. The particulate matter detection sensor has the structure as one aspect of the present invention previously described. Through the sensor connector, a wire harness such as sensor wires connected to the detection electrodes and heater wires connected to the heater are connected to an outside control device.

In the structure of the particulate matter detection sensor and unit according to the present invention, the temperature detection resistance is placed in the conductive path of the pair of the detection electrodes, and the first state and the second state can be switched. During the first state, no current flows through the temperature detection resistance. During the second state, a current flows in the temperature detection resistance.

In the first state, it is possible to detect the quantity of particulate matter accumulated between the detection electrodes, namely, the quantity of particulate matter contained in exhaust gas as target detection gas on the basis of the resistance between the detection electrodes.

In the second state, it is possible to detect the temperature of the sensor element on the basis of the sum of the resistance value between the detection electrodes and the resistance value of the temperature detection resistance. For example, the temperature of the sensor element corresponds to the difference between the resistance value obtained in the first state and the resistance value obtained in the second state. Accordingly, it is possible to adjust the sensor element at the optimum temperature in order to execute the detection process of detecting particulate matter on the basis of the detected temperature of the sensor element.

Further, because the first state and the second state can be switched in the structure in which the switching means is placed on the conductive path of the pair of the detection electrodes, it is possible to use the same wires when the temperature of the sensor element is detected and the quantity of particulate matter is detected. This makes it possible to decrease the total number of wires in the particulate matter detection sensor connected to an electric control unit as the control device which receives detection signals transferred from the particulate matter detection sensor.

Accordingly, it is possible to provide the particulate matter detection sensor capable of detecting the quantity of particulate matter and the temperature of the sensor element with a simple structure and a low manufacturing cost and without increasing the total number of components.

In the particulate matter detection sensor according to the present invention, the switching means is comprised of a capacitor. The capacitor is connected in series to the temperature detection resistance formed in the conductive path. The switching means receives one of a direct current signal (or a direct current voltage) and an alternating current signal (or an alternating current voltage) which are supplied from an electric power source to the pair of the detection electrodes. The switching means produces the first state when receiving the direct current signal which is supplied from the electric power source to the pair of the detection electrodes. The switching means produces the second state when receiving the alternating current signal which is supplied from the electric power source to the pair of the detection electrodes.

In particular, the capacitor as the switching means in the particulate matter detection sensor prevents the DC current from flowing in the temperature detection resistance when receiving the DC signal, and on the other hand allows the AC current to flow through the temperature detection resistance when receiving the AC signal. The structure of the particulate matter detection sensor according to the present invention makes it possible to easily switch the first state and the second state in order to make the electrical connection and disconnection of the temperature detection resistance.

In the particulate matter detection sensor according to the present invention, the capacitor is placed at a distal end of the sensor element and the temperature detection resistance is placed at a front side of the sensor element when observed along a longitudinal direction of the sensor element. The front side is opposite to the distal end along the longitudinal direction of the sensor element.

In general, because the capacitor as the switching means has relatively low heat resistance characteristics, deterioration and failure occur in the capacitor when it is placed in the exhaust gas pipe through which exhaust gas of a high temperature flows. Because the particulate matter detection sensor according to the present invention has the above structure in which the capacitor is placed at a position which is not affected from heat energy of the exhaust gas when the particulate matter detection sensor is placed in the exhaust gas pipe, it is possible to easily switch the first state and the second state and correctly detect the quantity of particulate matter and the temperature of the sensor element with high accuracy.

The resistance formed between the detection electrodes in the sensor element has the characteristics of temperature dependence which is changed depend on the change of the temperature of the sensor element.

The particulate matter detection sensor according to the present invention further has a heater. When receiving electric power, the heater generates heat energy in order to heat the sensor element. In the particulate matter detection sensor, the heater generates heat energy when receiving electric power supplied from the electric power source under a control by a control means on the basis of the temperature of the sensor element detected in the second state. This makes it possible to adjust the temperature of the sensor element at the optimum temperature while monitoring the actual temperature of the sensor element, and to detect the quantity of particulate matter accumulated between the detection electrodes in the sensor element with high accuracy.

As previously described, the resistance formed between the detection electrodes in the sensor element has the characteristics of temperature dependence which is changed depend on the change of the temperature of the sensor element. In general, the temperature of the sensor element is changed in response to the ambient environment. Even if the heater control is executed on the basis of the detected temperature of the sensor element, the temperature of the sensor element is changed according to the change of the temperature of the exhaust gas emitted from an internal combustion engine.

In the particulate matter detection sensor according to the present invention, because the temperature adjustment is executed to adjust the detected quantity of particulate matter accumulated between the detection electrodes which is calculated on the basis of the resistance value between the detection electrodes, it is possible to further increase the detection accuracy of detecting the quantity of particulate matter accumulated between the detection electrodes.

In the particulate matter detection sensor according to the present invention, wire breaking in the sensor element is detected on the basis of the resistance between the detection electrodes detected in the second state.

When wire breaking occurs in the sensor element of the particulate matter detection sensor, it is difficult to detect the resistance value between the detection electrodes. When no particulate matter is accumulated between the detection electrodes on the substrate of the sensor element, it is difficult to detect the resistance between the detection electrodes because no current flows in the temperature detection resistance. In this case, the resistance value between the detection electrodes takes infinitive value ($=\infty$). Accordingly, this means that it is difficult to detect whether or not wire breaking occurs in the sensor element on the basis of the detected resistance value because the following two cases (a) and (b) have the same resistance change during the first state:

(a) when no particulate matter is accumulated on the detection electrodes on the substrate; and (b) when wire breaking occurs in the sensor element.

On the other hand, even if no particulate matter is accumulated between the detection electrodes on the substrate of the sensor element, it is possible to detect the resistance value between the detection electrodes corresponding to the temperature of the sensor element because the structure of the particulate matter detection sensor according to the present invention to flow current in the temperature detection resistance during the second state. Accordingly, it is possible to detect the occurrence of wire breaking in the sensor element by using the particulate matter detection sensor according to the present invention.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Hereinafter, various embodiments of the present invention will be described with reference to the accompanying drawings. In the following description of the various embodiments, like reference characters or numerals designate like or equivalent component parts throughout the several diagrams.

Embodiment

A description will be given of a sensor element 13, a particulate matter (PM) detection sensor 10, a PM detection sensor unit equipped with the PM detection sensor 10, and a PM detection sensor system according to an embodiment of the present invention with reference to FIG. 1 to FIG. 9.

The particulate matter sensor system is mounted to an exhaust gas passage in an exhaust gas purifying system of an on-vehicle engine. The PM detection sensor system has the particulate matter detection sensor 10 according to the embodiment of the present invention. The PM detection sensor system has the PM detection sensor 10 in order to detect a quantity of conductive particulate matter (PM) contained in exhaust gas emitted from an on-vehicle engine. Such conductive particulate matter will also be referred to as the "particulate matter (PM)" in short.

For example, the on-vehicle engine is a diesel engine mounted to a motor vehicle. A diesel particulate filter (DPF) as the exhaust gas purifying device is mounted to an exhaust gas passage of the diesel engine. The DPF is capable of purifying exhaust gas emitted from the diesel engine. That is, the DPF captures particulate matter PM contained in the exhaust gas emitted from the diesel engine. The DPF is periodically regenerated in order to eliminate the particulate matter PM accumulated in the DPF on the basis of the detection result of the PM detection sensor. In such a DPF regeneration process, the DPF is fired at a high temperature in order to oxidize the accumulated particulate matter PM.

For example, the PM detection sensor is placed at the downstream of the DPF in the exhaust gas passage of the diesel engine. The PM quantity detection system calculates a quantity of particulate matter accumulated in the DPF on the basis of the output as the detection result of the PM detection sensor. When the calculated quantity of particulate matters exceeds a predetermined value, the DPF is regenerated. The PM detection sensor detects the quantity of particulate matter PM contained in the exhaust gas at the downstream of the DPF. It is possible to execute the faulty test of the DPF on the basis of the detection result of the PM detection sensor.

A description will now be given of a configuration of the PM detection sensor with the sensor element according to the embodiment of the present invention with reference to FIG. 1 and FIG. 2.

Figure 1:
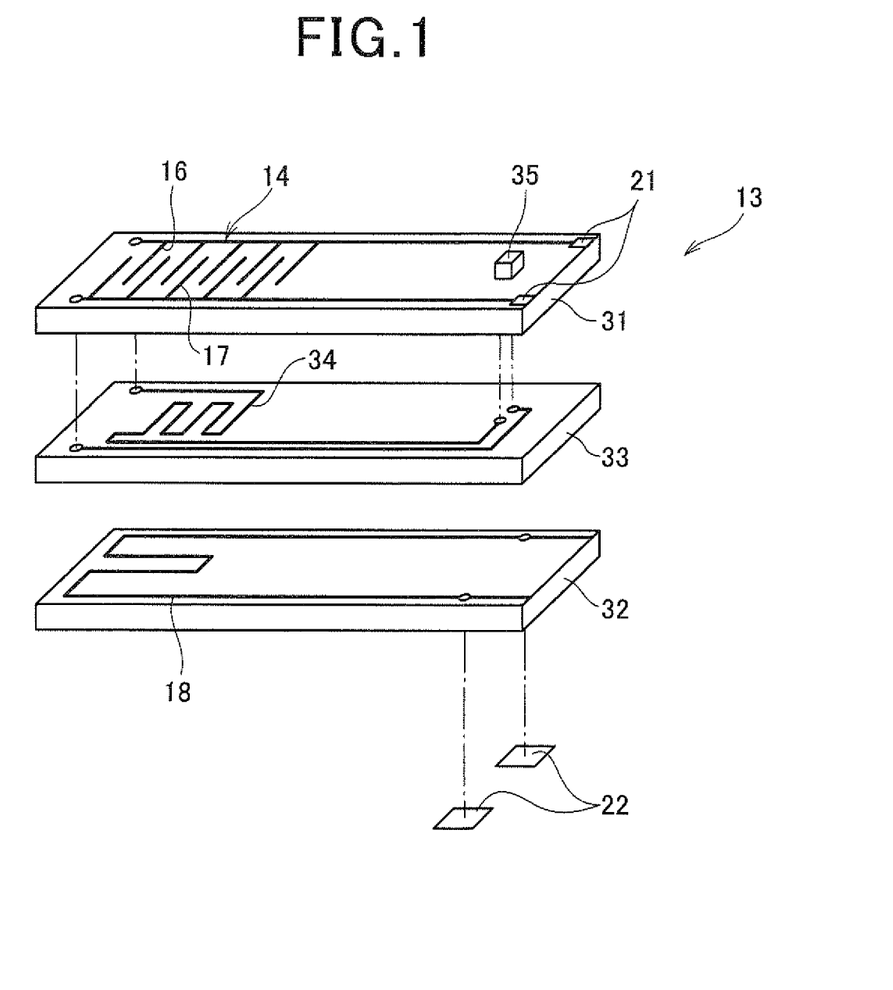
FIG. 1 is a perspective view showing a schematic structure of a sensor element to be placed in a particulate matter detection sensor according to an embodiment of the present invention.

FIG. 1 is a perspective view showing a schematic structure of the sensor element 13 which is placed in the particulate matter (PM) detection sensor 10 according to an embodiment of the present invention.

At first, a description will now be given of the entire structure of the PM detection sensor 10 with reference to FIG. 2.

Figure 2:
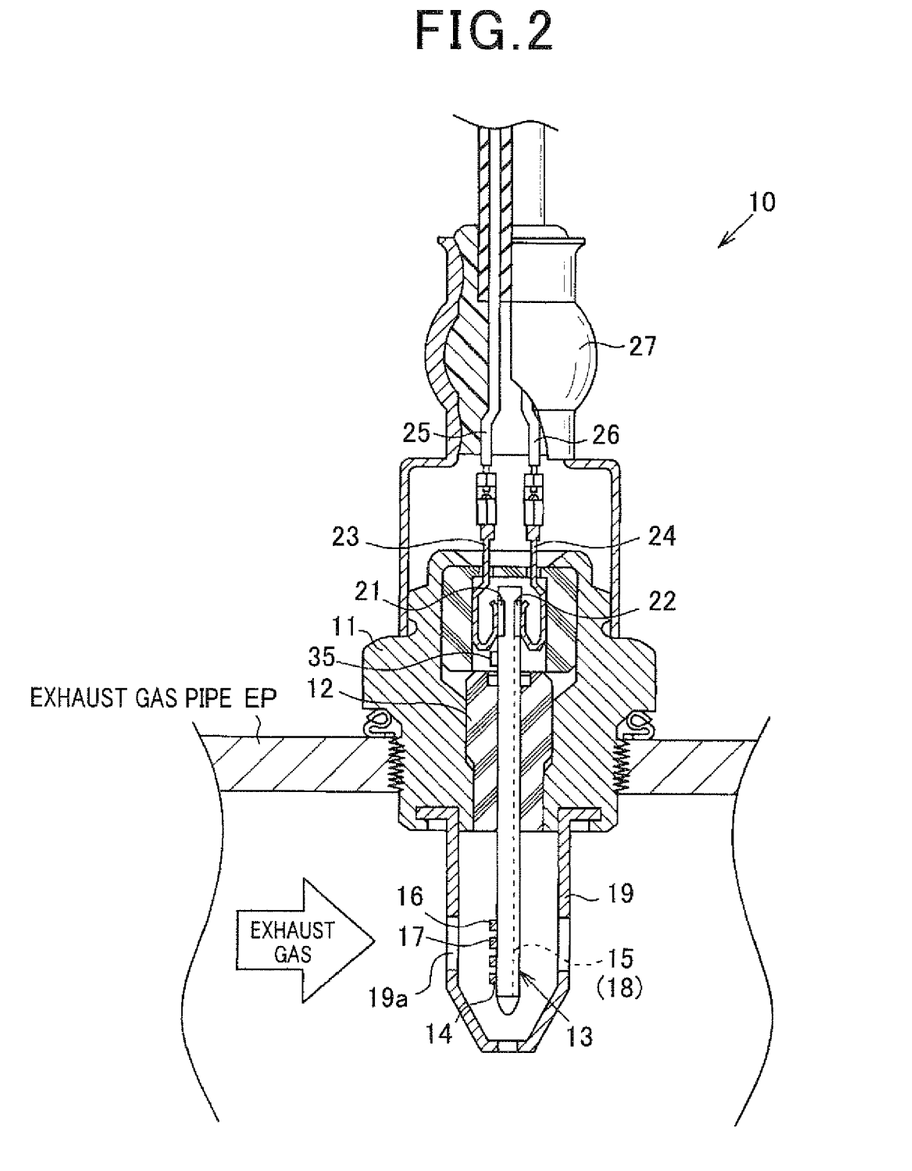
FIG. 2 is a view showing a cross section of the particulate matter detection sensor equipped with the sensor element according to the embodiment of the present invention.

FIG. 2 is a view showing a cross section of the PM detection sensor 10 according to the embodiment of the present invention.

As shown in FIG. 2, the PM detection sensor 10 has a housing case. In the housing case of the PM detection sensor 10, an insulator 12 of a cylindrical shape is placed. The sensor element 13 of a long plate shape is inserted in and supported by the insulator 12. The sensor element 13 is comprised of a PM detection part 14 and a heating part 15. The PM detection part 14 detects a quantity of particulate matter PM contained in exhaust gas as a target detection gas. The heating part 15 generates heat energy to heat the sensor element 13.

The PM detection part 14 is comprised of a pair of detection electrodes 16 and 17. The heating part 15 has a heater 18. The front part of the sensor element 13 extends from the insulator 13.

The PM detection part 14 (having the detection electrodes 16 and 17) is formed at the front part of the sensor element 13. The cover body 19 covers the entire of the projection part of the sensor element 13. The sensor element 13 is placed in the inside of the cover body 19.

A terminal 21 and a terminal 22 are placed at the distal end of the sensor element 13. The distal end of the sensor element 13 is opposite in position to the PM detection part 14 in the longitudinal direction of the PM detection sensor 10. The terminal 21 is connected to the detection electrodes 16 and 17. The terminal 22 is connected to the heater 18.

The terminals 21 and 22 are connected to metal fittings 23 and 24, respectively. The terminals 21 and 22 are connected to sensor wires, that is, a signal wire 25 and a heater wire 26, respectively, through the connection metal fittings 23 and 24.

The sensor wires 25 and 26 are connected to a control device (omitted from FIG. 1 and FIG. 2) through vehicle wires. The control device is placed at the outside of the casing 27 of the PM detection sensor 10.

The PM detection sensor 10 is attached to the wall of the exhaust gas pipe EP through the housing case 11 of the PM detection sensor 10. When the PM detection sensor 10 is fixed to the exhaust gas pipe EP through the housing case 11, the front part of the sensor element 13 is placed in the inside of the exhaust gas pipe EP through which exhaust gas as the target detection gas flows. That is, the PM detection part 14 (having the detection electrodes 16 and 17) is placed approximately at the central part of the inner space of the exhaust gas pipe EP so that the sensor element 13 faces the upstream side of the exhaust gas flow. A plurality of holes is formed in the cover body 19, through which the exhaust gas is introduced into the inside of the sensor element 13.

Next, a description will now be given of the sensor element 13 with reference to FIG. 1. FIG. 1 is a partial perspective view showing a schematic structure of the sensor element 13.

The sensor element 13 is comprised of three substrates 31, 32 and 33 made of electrical insulation heat resistance material. The three substrates 31, 32 and 33 are stacked. The detection electrodes 16 and 17 are formed on a part of the first substrate 31 which corresponds to the front end part of the PM detection sensor 10. The detection electrodes 16 and 17 form the PM detection part 14. Each of the detection electrodes 16 and 17 has a comb structure. The teeth of the detection electrode 16 and the teeth of the detection electrode 17 face to each other and are alternately placed at a predetermined gap. Each of the detection electrodes 16 and 17 is placed so that the comb teeth are arranged along the longitudinal direction of the PM detection part 14. The terminal 21 is formed on the other surface of the first substrate 31, which is opposite to the surface on which the detection electrodes 16 and 17 are formed.

The shape of the pair of the detection electrodes 16 and 17 is not limited by the structure previously described. It is possible for the detection electrodes 16 and 17 to have a structure in which the comb teeth of each of the detection electrodes 16 and 17 are arranged along a direction which is perpendicular to the longitudinal direction of the sensor element 13 or a structure in which each of the teeth of the detection electrodes 16 and 17 has a spiral shape.

The heater 18 is formed on the second substrate 32. The heater 18 is composed of heating wires. Like the detection electrodes 16 and 17, the heater 18 is placed at the front end of the sensor element 13. The terminal 22 is formed on the surface of the second substrate 32, which is opposite to the surface on which the heater 18 is formed. The heater 18 is electrically connected to the terminal part 22 through a through hole electrode (not shown) which is formed in the second substrate 32.

In the sensor element 13, the first substrate 31 is a front substrate, and the second substrate is a back substrate. The PM detection sensor 10 is placed in the exhaust gas pipe EP so that the first substrate 31 faces the upstream side of the exhaust gas flow, and the second substrate 32 faces the downstream side of the exhaust gas flow in the exhaust gas pipe EP. This arrangement of the PM detection sensor 10 in the exhaust gas pipe EP makes it possible to adhere particulate matter PM to the detection electrodes 16 and 17 and peripheral area of the detection electrodes 16 and 17 formed on the first substrate 31. The particulate matter PM is accumulated on the detection electrodes 16 and 17 and the peripheral part.

The third substrate 33 is placed between the first substrate 31 and the second substrate 32. A temperature detection resistance 34 is formed on the third substrate 33. The temperature detection resistance 34 acts as a temperature detection element capable of detecting the temperature of the sensor element 13. Like the detection electrodes 16 and 17 and the heater 18, the temperature detection resistance 34 is placed at the front end in the longitudinal direction of the sensor element 31. The temperature detection resistance 34 is also placed in the inside of the exhaust gas pipe EP when the PM detection sensor 10 is placed in the exhaust gas pipe EP. The temperature detection resistance 34 is placed between the heater 18 and the pair of the detection electrodes 16 and 17.

A capacitor 35 is formed on the first substrate 31. The capacitor 35 is connected in series to the temperature detection resistance 34 through the through hole (not shown) formed in the first substrate 31. The capacitor 35 corresponds to a switching means used in the claims, which is capable of making a first state and a second state which make the electric connection and disconnection to the temperature detection resistance 34. The first state and the second state will be explained later in detail.

The detection electrodes 16 and 17 are formed at one end part of the first substrate 31 along the longitudinal direction of the sensor element 13 and the capacitor 35 is formed at the other end part of the first substrate 31 along the longitudinal direction of the sensor element 13. In other words, as shown in FIG. 2, the capacitor 35 is placed on the first substrate 31 at the outside of the exhaust gas pipe EP which is not adversely influenced by heat energy supplied from the exhaust gas.

The temperature detection resistance 34 and the capacitor 35 make a series circuit. The series circuit is connected to the PM detection part 14. That is, one end terminal of the series circuit composed of the temperature detection resistance 34 and the capacitor 35 is connected to the detection electrode 16 in the PM detection part 14 and the other end terminal thereof is connected to the detection electrode 17 in the PM detection part 14. In particular, the series circuit composed of the temperature detection resistance 34 and the capacitor 35 is connected to the front end (as the front end part of a pair of printed wires extending along the longitudinal direction of the sensor element 13) of the detection electrodes 16 and 17.

The series circuit composed of the temperature detection resistance 34 and the capacitor 35 is connected to the detection electrodes 16 and 17 through the through hole (not shown) formed in the first substrate 31.

The series circuit composed of the temperature detection resistance 34 and the capacitor 35 on the third substrate 33 is formed between the pair of the detection electrodes 16 and 17 formed on the first substrate 31. In other words, the temperature detection part having the temperature detection resistance 34 is formed in parallel to the PM detection part 14 in the sensor element 13.

The capacitor 35 prevents a direct current signal (or a DC voltage) from flowing therein, and allows an alternate current signal (AC signal) to flow.

When the DC signal is supplied to the sensor element 13, the above circuit structure makes a current flow path containing the PM detection part 14 and not containing the temperature detection part composed of the temperature detection resistance 34 and the capacitor 35.

On the other hand, when the AC signal is supplied to the sensor element 13, the above circuit structure makes a current flow path containing the PM detection part 14 and the temperature detection part composed of the temperature detection resistance 34 and the capacitor 35.

The condition when the DC signal is supplied to the sensor element 13 corresponds to a first status in which no current flows in the temperature detection resistance 34. The condition when the AC signal is supplied to the sensor element 13 corresponds to a second status in which a current flows in the temperature detection resistance 34.

In the PM detection sensor 10 having the above structure according to the embodiment of the present invention, a resistance value of the PM detection part 14 (that is a resistance between the detection electrodes 16 and 17) is changed by the quantity of particulate matter PM contained in exhaust gas accumulated on the first substrate 31 of the sensor element 13. The resistance change rate is in proportional to the quantity change of particulate matter PM accumulated between the detection electrodes 16 and 17 formed on the first substrate 31.

The PM quantity detection system according to the embodiment of the present invention is comprised of an electric control unit (ECU). The ECU calculates the quantity of particulate matter PM contained in exhaust gas as the target detection gas on the basis of the detection result of the resistance between the detection electrodes 16 and 17.

Figure 3:
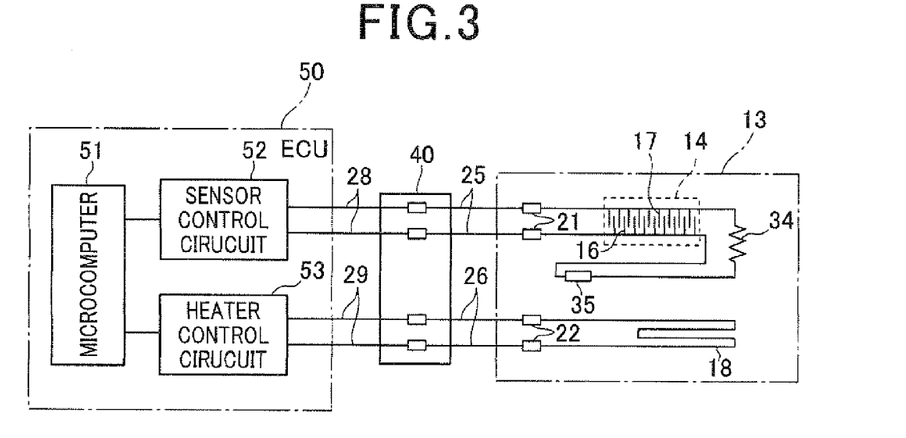
FIG. 3 is a view showing the entire structure of a PM detection sensor system using the particulate matter detection sensor according to the embodiment of the present invention.

FIG. 3 is a view showing an entire structure of a particulate matter PM quantity detection system using the particulate matter detection sensor according to the embodiment of the present invention.

As shown in FIG. 3, the sensor wires 25 and 26 of the PM detection sensor 10 are connected to the terminals of the ECU 50 through vehicle wires 28 and 29, respectively. A sensor connector 40 is placed at the opposite position to the connection part between the sensor element 13 and the ECU 50. Through the sensor connector 40, the sensor wires 25 and 26 are electrically connected to the vehicle wires 28 and 29, respectively. In general, the sensor wires 25 and 26 are short in length, compared to the vehicle wires 28 and 29. For example, each of the sensor wires 25 and 16 has approximately 0.5 m long, and each of the vehicle wires 28 and 29 has approximately 5 m long.

The ECU 50 is an on-vehicle ECU comprised of a microcomputer 51. The microcomputer 51 adjusts a quantity of fuel injection on the basis of the operation condition of the internal combustion engine mounted to the vehicle. The ECU 50 is comprised of a sensor control circuit 52 and a heater control circuit 53. The detection signal of the PM detection sensor 10 is transferred to the microcomputer 51 through the sensor control circuit 52. The microcomputer 51 calculates the quantity of particulate matter PM accumulated in the PM detection sensor 10 on the basis of the detection result of the PM detection sensor 10. When the calculated quantity of particulate matter PM exceeds a predetermined judgment value, the microcomputer 51 executes the regeneration of the DPF. The microcomputer 51 further calculates the quantity of particulate matter PM contained in exhaust gas at the downstream side of the DPF on the basis of the detection result of the PM detection sensor 10. When the detection result exceeds a predetermined judgment value, the microcomputer 51 judges the occurrence of DPF failure.

Figure 4:
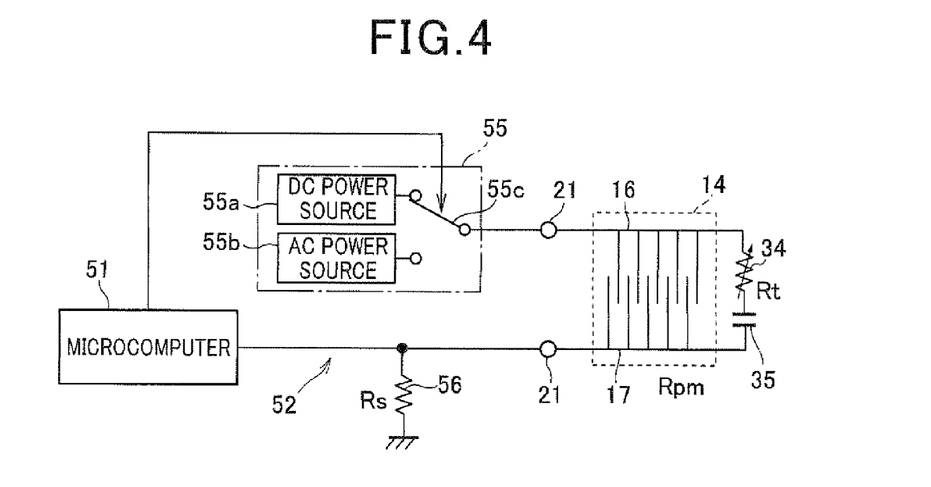
FIG. 4 is a view showing a configuration of a sensor control circuit in the PM detection sensor system shown in FIG. 3.

FIG. 4 is a view showing a configuration of the sensor control circuit 52 in the particulate matter PM quantity detection system shown in FIG. 3.

As shown in FIG. 4, the sensor control circuit 52 is comprised of an electric power source 55 and a detection resistance 56. The electric power source 55 supplies an electric power voltage to the sensor element 13 in the PM detection sensor 10. Through the detection resistance 56, the ECU 50 detects a resistance value Rpm of the PM detection part 14 (namely, a resistance value between the detection electrodes 16 and 17) in the sensor element 13 when the electric power source 55 supplies the electric power voltage to the sensor element 13 in the PM detection sensor 10.

The resistance value Rpm between the detection resistances 16 and 17 in the PM detection part 14 is changed according to the change of quantity of particulate matter PM accumulated between the detection resistances 16 and 17. The change of the resistance value Rpm is detected as the divided voltage in the dividing circuit comprised of the PM detection part 14 and the detection resistance 56. That is, the microcomputer 51 in the ECU 50 receives the PM detection voltage which is the voltage Rs at the connection node A between the PM detection part 14 and the detection resistance 56.

For example, in a case in which the resistance value Rpm of the PM detection part 14 is changed within a range of infinity (PM accumulated value=0) to 1 k$\Omega$, when the detection resistance 56 is 100 k$\Omega$ (Rs=100 k$\Omega$), and the electric power source 55 supplies 5 V of a DC voltage, and the PM accumulated value in the PM detection part 14 is zero, $$PM \text{ detection voltage} = 5 \text{ V} \times 100 \text{ k}\Omega / (100 \text{ k}\Omega + \infty)$$

$$= 0 \text{ V}.$$

When the resistance value Rpm of the PM detection part 14 is 1 k$\Omega$ (PM accumulated value=1 k$\Omega$), $$PM \text{ detection voltage} = 5 \text{ V} \times 100 \text{ k}\Omega / (100 \text{ k}\Omega + 1 \text{ k}\Omega)$$

$$= 4.95 \text{ V}.$$

Because the PM detection voltage is changed in accordance with the change of the quantity of particulate matter PM accumulated between the detection resistance 16 and 17, the microcomputer 51 monitors the quantity of particulate matter PM accumulated between the detection resistances 16 and 17 in the PM detection part 14 of the sensor element 13 on the basis of particulate matter PM accumulated between the detection resistances 16 and 17 in the PM detection part 14.

The sensor element 13 has the temperature detection part (which is composed of the temperature detection resistance 34 and the capacitor 35) which is placed in parallel to the PM detection part 14. The sensor element 13 has the first state and the second state which can be switched. The capacitor 35 makes the first state and the second state. In the first state, no current flows in the temperature detection resistance 34 by the presence of the capacitor 35. In the second state, a current flows in the temperature detection resistance 34 by the presence of the capacitor 35. The first state and the second state can be switched by flowing a direct current signal (DC signal) and an alternate current signal (AC signal) to the sensor element 13.

A description will now be given of the process of switching the first and second states.

The electric power source device 55 is comprised of a DC power source part 55*a*, an AC power source part 55*b* and a switch part 55*c*.

The DC power source part 55*a* generates a DC voltage. The AC power source generates an AC voltage. The switch part 55*c* selects one of the DC voltage and the AC voltage and supplies the selected voltage to the sensor element 13. The DC power source 55*a* is a DC voltage output circuit which outputs 5 V of DC voltage, for example. The AC power source 55*b* is an AC voltage output circuit which outputs ±5 V of AC voltage, for example.

When the DC power source 55*a* in the electric power source device 55 supplies the DC voltage to the sensor element 13, no current flows in the temperature detection resistance 34 by the capacitor 35. Accordingly, the resistance of the sensor element 13, namely, the resistance between the terminals 21 (namely, between the detection electrodes 17 and 18) is the resistance Rpm of the PM detection part 14. In this case, the PM detection voltage is supplied to the microcomputer 51. The PM detection voltage is determined by the resistance value Rpm of the PM detection part 14 and the resistance value Rs of the detection resistance 56.

On the other hand, when the AC power source 55*b* in the electric power source device 55 supplies the AC voltage to the sensor element 13, a current flows in the temperature detection resistance 34 by the presence of the capacitor 35, the resistance value of the sensor element 13, namely, the resistance value between the terminals 21 (namely, between the detection electrodes 17 and 18) is the sum of the resistance value Rpm of the PM detection part 14 and the resistance value Rt of the temperature detection resistance 34. In this case, the PM detection voltage is supplied to the microcomputer 51. The PM detection voltage is determined by the resistance value Rs of the detection resistance 56 and the total sum of the resistance value of the PM detection part 14 and the temperature detection resistance 34.

When the DC voltage is supplied to the sensor element 13, the PM detection voltage becomes the voltage signal which is determined by the resistance value Rpm of the PM detection part 14 as the changeable resistance component. On the other hand, when the AC voltage is supplied to the sensor element 13, the PM detection voltage becomes the voltage signal which is determined by the resistance value Rpm of the PM detection part 14 as the changeable resistance component and the resistance value Rt of the temperature detection resistance 34. It is therefore possible for the microcomputer 51 in the ECU 50 to calculate an actual temperature of the sensor element 13 in addition to the quantity of particulate matter PM accumulated in the sensor element 13.

Because the PM detection voltage is detected as an AC signal when the AC voltage is supplied to the sensor element 13, it is possible to eliminate an AC component from the PM detection voltage by a low pass filter. The microcomputer 51 calculates the quantity of particulate matter PM contained in the sensor element 13 on the basis of the PM detection voltage without AC component.

The microcomputer 51 transfers a switch control signal to the switch part 55*c* in the electric power source device 55 in order to switch the state of the switch part 55*c*. In this case, after the DC power source part 55*a* supplies the DC voltage (or the DC signal) to the sensor element 13, the microcomputer 51 instructs the switch part 55*c* to switch its state so that the AC power source part 55*b* supplies the AC voltage (or the AC signal) to the sensor element 13 at the optimum timing (for example, every 128 msec) so as to execute the temperature control of the sensor element 13.

The microcomputer 51 instructs the heater 18 to generate heat energy so as to maintain the temperature of the sensor element 13 constant and suppress the sensor element 13 from being overheated. This control makes it possible to enter the sensor element 13 in the good condition of maintaining the temperature of the sensor element 13 to capture particulate matter PM contained in the exhaust gas as the target detection gas with high accuracy. Specifically, the microcomputer 51 executes a feedback control so as to maintain the sensor element 13 at the target temperature Ts (for example, Ts=200° C.).

During the execution of the feedback control, the microcomputer 51 calculates a duty ratio of the electric power supply to the sensor element 13 on the basis of a difference between the temperature Ts and the target temperature Ttg, where the temperature Ts is the actual temperature of the sensor element 13 obtained by the temperature detection resistance 34.

The microcomputer 51 executes the electric power supplying control to the heater 18 on the basis of the calculated duty ratio. That is, the microcomputer 51 executes the temperature control of the sensor element 13 on the basis of the temperature Ts of the sensor element detected by using the temperature detection resistance 34.

By the way, the resistance Rpm of the PM detection part 14 has the temperature-dependent characteristics. Therefore even if the particulate matter PM accumulated in the sensor element 13 is a constant value, the resistance value Rpm of the PM detection part 14 is changed according to the change of the temperature of the sensor element 13. That is, even if the resistance value Rpm of the detection part 14 takes a constant value, the particulate matter PM accumulated in the sensor element 13 is changed by the temperature of the sensor element 13.

On the other hand, because the sensor element 13 is placed in the inside of the exhaust gas pipe EP, the temperature of the sensor element 13 is changed according to the change of the temperature of the exhaust gas. During the transition of temperature change of the exhaust gas, even if the microcomputer 51 executes the temperature feedback control, there often causes a difference between the actual temperature of the sensor element 13 and the target temperature. During such a transition state of the temperature of the exhaust gas, it is difficult to detect the quantity of particulate matter PM accumulated in the sensor element 13 with high accuracy.

In the embodiment of the present invention, the microcomputer 51 calculates the quantity of particulate matter PM accumulated in the sensor element 13, and adjusts the calculated quantity on the basis of the temperature Ts of the sensor element 13. The microcomputer 51 in the ECU 50 executes the DPF regeneration control and the DPF fault diagnosis on the basis of the adjusted quantity of particulate matter PM accumulated in the sensor element 13.

Specifically, the microcomputer 51 calculates a basic quantity of particulate matter PM on the basis of the basic characteristics when the sensor element 13 has a predetermined temperature, that is, on the basis of the resistance value Rpm currently detected by using the relationship between the resistance value Rpm of the PM detection part 14 and the quantity of particulate matter PM accumulated in the sensor element 13. The microcomputer 51 further adjusts the basic quantity of particulate matter PM by using an adjusting coefficient calculated on the basis of the temperature of the sensor element 13. (Quantity of particulate matter PM accumulated in the sensor element 13=Basic quantity of particulate matter PM×Adjusting coefficient)

The adjusting coefficient is determined so that the more the temperature Ts of the sensor element 13 is increased, the more the resistance value of particulate matter PM accumulated between the detection electrodes 16 and 17 is decreased. Further, the adjusting coefficient is determined on the basis of the feature in which the more the temperature Ts of the sensor element 13 is increased, the more the resistance Rpm of the PM detection part 14 is decreased even if the actual quantity of particulate matter PM accumulated is not changed.

Figure 5:
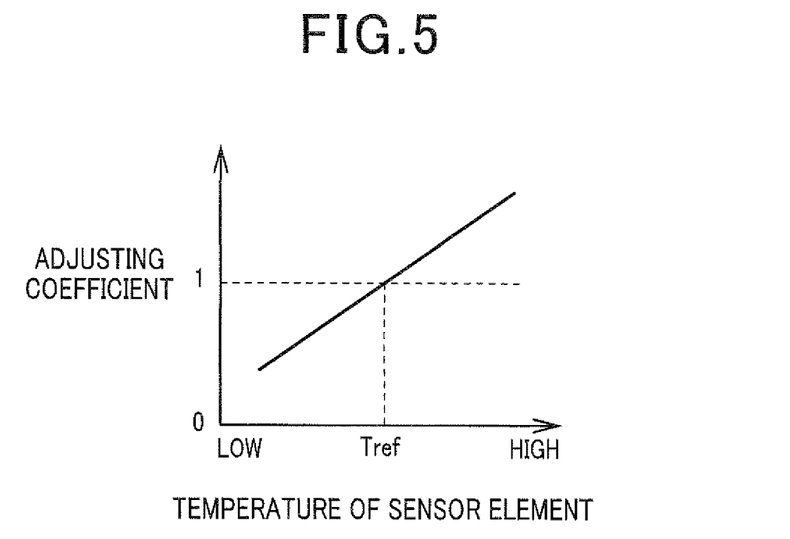
FIG. 5 is a view showing a map of adjusting the quantity of particulate matter.

FIG. 5 is a view showing a map of adjusting the quantity of particulate matter PM. The map shows one example for calculating the adjusting coefficient. In the map shown in FIG. 5, the adjusting coefficient takes the value of 1 when the sensor element 13 has the reference element temperature Tref. When the temperature of the sensor element 13 is higher than the reference temperature Tref, the adjusting coefficient takes a value of more than 1. On the other hand, when the temperature is lower than the reference temperature Tref, the adjusting coefficient takes a value of less than 1.

The reference element temperature Tref is a target temperature of the control process of supplying the electric power to the heater 18.

In the map shown in FIG. 5, when the temperature Ts of the sensor element 13 is higher than the reference temperature Tref, the microcomputer 51 in the ECU 50 increases the value of the basic quantity of particulate matter PM. On the other hand, when the temperature Ts of the sensor element 13 is lower than the reference temperature Tref, the microcomputer 51 in the ECU 50 decreases the value of the basic quantity of particulate matter PM.

When the actual quantity of particulate matter PM accumulated in the sensor element 13 is changed, it can be considered that the resistance value Rpm (PM detection voltage) corresponding to the temperature of the sensor element 13 is changed. In order to increase the detection accuracy of detecting the quantity of particulate matter PM accumulated in the sensor element 13, it is necessary to prepare maps corresponding to the resistance value Rpm (Pm detection voltage), and to switch the maps in accordance with the actual resistance value Rpm (PM detection voltage).

When the calculated value of accumulated particulate matter PM reaches the predetermined value after the actual quantity of particulate matter PM accumulated in the sensor element 13 is increased, the microcomputer 51 in the ECU 50 executes the DPF regeneration process. At this time the microcomputer 51 further executes the PM regeneration process of the PM detection sensor 10. That is, the microcomputer 51 executes the PM firing control in which particulate matter PM accumulated in the sensor element 13 is fired and oxidized at a high temperature when the calculated quantity of particulate matter PM accumulated in the sensor element 13 exceeds the predetermined value. Specifically, the microcomputer 51 sets the target temperature Tt temporarily to PM firing temperature (for example, 800° C.) when the calculated quantity of particulate matter PM accumulated in the sensor element 13 reaches the predetermined value. At this time, the microcomputer 51 instructs the heater control circuit 53 to supply electric power to the heater 18. When receiving the electric power, the heater 18 generates heat energy. The heat energy of the heater 18 increases the temperature Ts of the sensor element 13 in order to eliminate accumulated particulate matter PM from the sensor element 13.

Next, a description will be given of the process of detecting accumulated particulate matter PM, the process of detecting the temperature of the sensor element 13, and the process of supplying electric power to the heater 1 with reference to FIG. 6.

Figure 6:
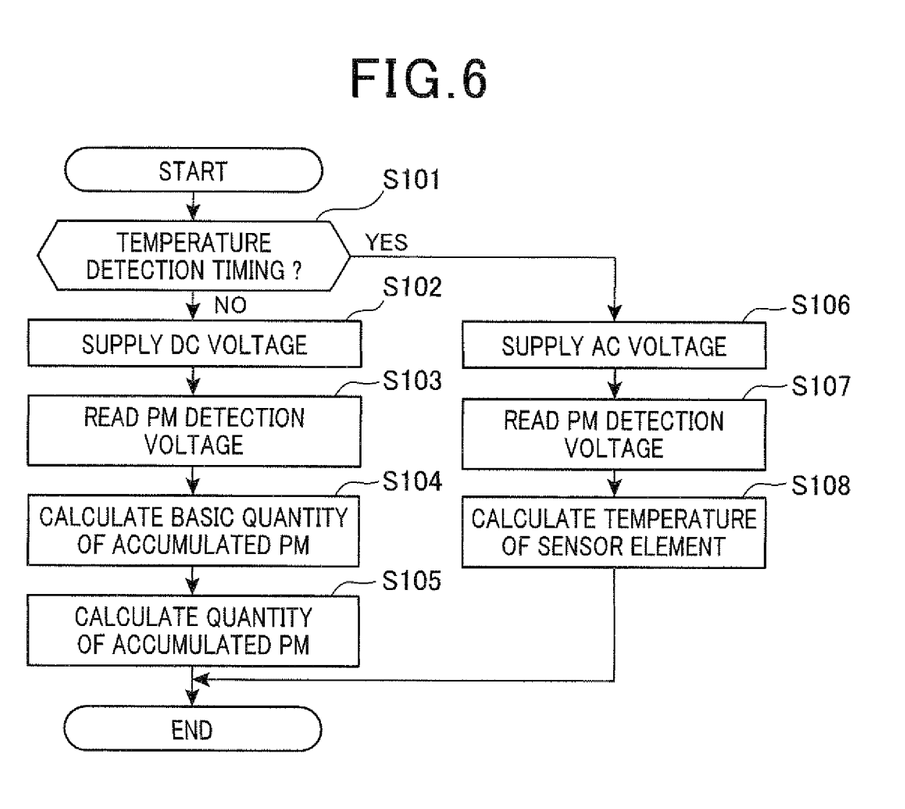
FIG. 6 is a flow chart showing the process of detecting a quantity of particulate matter PM accumulated in the sensor element and the process of detecting a temperature of the sensor element according to the embodiment of the present invention.

FIG. 6 is a flow chart showing the process of detecting the quantity of particulate matter PM accumulated in the sensor element 13 and the process of detecting the temperature of the sensor element 13 according to the embodiment of the present invention.

The microcomputer 51 in the ECU 50 executes the processes shown in FIG. 6 every predetermined period of time (for example, every 4 msec).

As shown in FIG. 6, the microcomputer 51 detects whether or not now is of the time for detecting the temperature of the PM detection sensor 10 (step S101). The embodiment uses the temperature detecting timing every period of 128 msec, for example.

When the detection result in step S101 indicates negation ("NO" in step S101), the operation flow goes to step S102. In step S102, the microcomputer 51 instructs the electric power source 55 to supply the DC voltage to the sensor element 13. At this time, when the current state of the switch part 55c is connected to the AC electric power source 55b and the AC voltage is supplied to the sensor element 13, the microcomputer 51 instructs the switch part 55c to connect the DC power source to the sensor element 13.

After the step S102, the operation flow goes to step S103. In step S103, the microcomputer 51 reads the PM detection voltage (the resistance Rpm detection value of the PM detection part 14) when the DC voltage is supplied to the sensor element 13. The operation flow goes to step S104.

In step S104, the microcomputer 51 calculates the basic particulate matter PM accumulated value on the basis of the PM detection voltage. The operation flow goes to step S105.

In step S105, the microcomputer 51 adjusts the basic particulate matter PM accumulated value using the adjusting coefficient which is obtained on the basis of the temperature of the sensor element 13 at this time (the quantity of accumulated particulate matter PM=basic particulate matter PM accumulated value×adjusting coefficient). At this time, the microcomputer 51 reads the previous temperature detection value previously detected (in step S108, will be explained later) as the temperature of the PM detection sensor 13. The microcomputer 51 calculates the adjusting coefficient from the map shown in FIG. 5.

On the other hand, when the detection result in step S101 indicates affirmation ("YES" in step S101), the operation flow goes to step S106. In step S106, the microcomputer 51 instructs the electric power source device 55 to supply the AC voltage to the sensor element 13. At this time, when the current state of the switch part 55c is connected to the DC electric power source 55a and the DC voltage is supplied to the sensor element 13, the microcomputer 51 instructs the switch part 55c to connect the AC power source to the sensor element 13.

After the step S106, the operation flow goes to step S107. In step S107, the microcomputer 51 reads the PM detection voltage (the resistance Rpm detection value of the PM detection part 14) when the AC voltage is supplied to the sensor element 13. The operation flow goes to step S108.

In step S108, the microcomputer 51 calculates the temperature of the sensor element 13 on the basis of the PM detection voltage. In particular, when the AC voltage is supplied to the sensor element 13, the PM detection voltage contains the detection component of the temperature of the sensor element 13, that is, the PM detection voltage corresponds to the sum of the resistance value Rpm of the PM detection part 14 and the resistance value Rt of the temperature detection resistance 34.

The microcomputer 51 calculates the temperature of the sensor element 13 on the basis of the PM detection voltage (the value read in step S103) when the DC voltage is supplied to the sensor element 13 and the PM detection voltage (the value read in step S107) when the AC voltage is supplied to the sensor element 13.

A description will now be given of the process of supplying electric power to the heater 18 with reference to FIG. 7.

Figure 7:
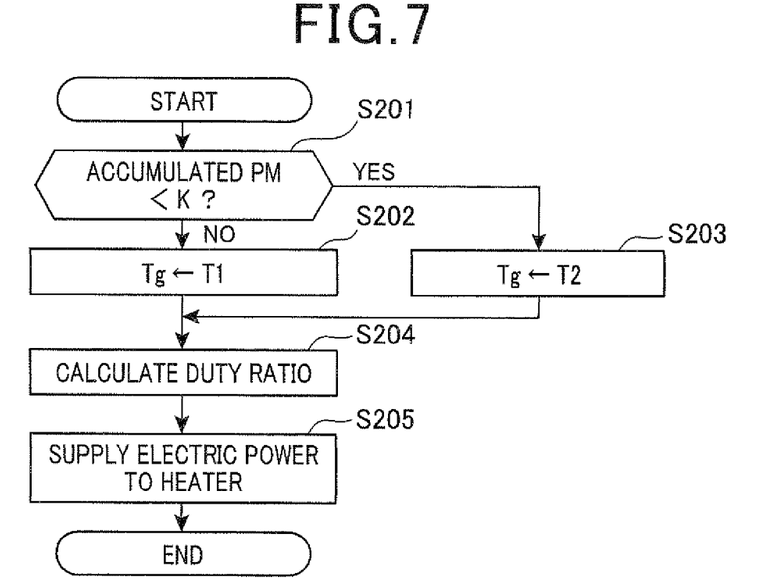
FIG. 7 is a flow chart showing the process of supplying electric power to a heater in the particulate matter detection sensor according to the embodiment of the present invention in order to eliminate particulate matter accumulated in the sensor element shown in FIG. 1.

FIG. 7 is a flow chart showing the process of supplying the electric power to the heater 18 in the particulate matter PM detection sensor according to the embodiment of the present invention in order to eliminate particulate matter accumulated in the sensor element shown in FIG. 1.

The microcomputer 51 in the ECU 50 executes the process shown in FIG. 7 every predetermined period of time.

As shown in FIG. 7, in step S201, the microcomputer 51 detects whether or not the calculated quantity of particulate matter PM accumulated in the sensor element 13 (as the calculation value in step S105) is less than the predetermined quantity K.

When the detection result in step S201 indicates affirmation (calculated quantity of particulate matter PM accumulated in the sensor element 13<the predetermined quantity K) ("YES" in step S202), the operation flow goes to step S202.

On the other hand, when the detection result in step S201 indicates negation (which indicates that the calculated quantity of particulate matter PM accumulated in the sensor element 13>=the predetermined quantity K) ("NO" in step S202), the operation flow goes to step S203. The predetermined quantity K is a judgment value whether or not the process of eliminating accumulated particulate matter PM from the sensor element 13 is executed by firing.

In step S202, the microcomputer 51 sets the target temperature Ttg of the sensor element 13 to a usual target temperature T1 (for example, 200° C.).

On the other hand, in step S203, the microcomputer 51 sets the target temperature Ttg to a high target temperature T2 (for example, 800° C.) which is more than the usual target temperature T1. The accumulated particulate matter PM can be eliminated from the sensor element 13 at the high target temperature T2.

After this, in step S204, the microcomputer 51 calculates a duty ratio of the supply of electric power to the heater 18 on the basis of the difference between the target temperature Ttg and the actual temperature (temperature of the sensor element 13). The operation flow goes to step S205. In step S205, the microcomputer 51 instructs the heater control circuit 53 to supply electric power to the heater 18 on the basis of the calculated duty ratio.

It is possible to use a predetermined value K as a judgment value whether or not the DPF regeneration process is executed. In this case, when the quantity of particulate matter PM accumulated in the sensor element 13 reaches the predetermined value K, the microcomputer 51 executes the DPF regeneration process, and further executes the process of eliminating accumulated particulate matter PM from the sensor element 13.

A description will now be given of the effects of the PM detection sensor 13, the PM detection sensor unit 10, and the PM detection sensor control system according to the embodiment of the present invention.

The structure of the PM detection sensor according to the present invention has the temperature detection resistance 34 in addition to the pair of the detection electrodes 16 and 17. Further, the microcomputer 51 in the ECU 50 instructs the electric power source device 55 to supply one of the DC voltage and the AC voltage in order for the capacitor 35 to make the first state and the second state. In the first state, the switch part 55c, no current flows in the temperature detection resistance 34. On the other hand, in the second state, current flows in the temperature detection resistance 34.

Accordingly, when the switch part 55c selects supplying the DC voltage in order for the capacitor 35 to make the first state because the capacitor 35 prevents current from flowing in the temperature detection resistance 34, it is possible for the microcomputer 51 to detect the quantity of particulate matter PM contained in exhaust gas as the target detection gas on the basis of the resistance value Rpm between the detection electrodes 16 and 17.

Further, when the switch part 55c selects supplying the AC voltage in order for the capacitor 35 to make the second state because the capacitor 35 allows current from flowing in the temperature detection resistance 34, it is possible for the microcomputer 51 to detect the temperature of the sensor element 13 on the basis of the total sum of the resistance value Rpm between the detection electrodes 16 and 17 and the resistance value Rt of the temperature detection resistance 34. That is, it is possible to obtain the temperature of the sensor element 13 on the basis of the difference between the resistance value (the resistance value between the detection electrodes 16 and 17) obtained in the first state and the resistance value (the total sum of the resistances previously described) obtained in the second state. Accordingly, it is possible to control the temperature of the sensor element 13 to the optimum temperature on the basis of the detection temperature.

Further, the PM detection sensor 10 according to the present invention has the configuration in which the temperature detection resistance 34 is placed in the conductive path of the pair of the detection electrodes 16 and 17 and the process of switching the power supply previously described, it is possible to use the wires used by the temperature detection of the PM detection sensor as the wires of detecting the accumulated quantity of particulate matter PM. This makes it possible to decrease the total length of the wires between the PM detection sensor 10 and the ECU 50 as the control device of receiving the detection signals transferred from the PM detection sensor. The present invention provides the PM detection system capable of detecting the accumulated quantity of particulate matter PM and detecting the temperature of the sensor element 13 with a simple configuration without increasing the production cost caused by increasing the number of components thereof.

The microcomputer 51 in the ECU 50 executes the first and second state switching operation by using the capacitor 35 and the electric power supply device 55. The capacitor 35 is placed in series to the temperature detection resistance 34 in the conductive path which is formed between the pair of the detection electrodes 16 and 17. According to the control of the microcomputer 51, the electric power supply device 55 supplies one of the AC voltage and the DC voltage to the pair of the detection electrodes 16 and 17. Therefore the capacitor 35 makes it possible to prevent the DC current from flowing in the capacitor 35 and the temperature detection resistance 34 and to allow the AC current to flow in the capacitor 35 and the temperature detection resistance 34. Therefore no current flows in the temperature detection resistance 34 when the DC voltage is supplied to the pair of the detection electrodes 16 and 17 in the first state. On the other hand, the current flows in the temperature detection resistance 34 when the AC voltage signal is supplied to the pair of the detection electrodes 16 and 17 in the second state. It is therefore possible to easily switch the permission and inhibition to flow the current in the temperature detection resistance 34.

The capacitor 35 is placed at the outside position of the exhaust gas pipe EP which is far from the heat affected zone. This structure makes it possible to suppress the capacitor 35 from being deteriorated and causing defect by the heat energy of the exhaust gas. Further, it is possible from the microcomputer 51 to easily and efficiently execute the switching between the first state and the second state previously described.

Further, because the resistance value Rpm between the detection electrodes 16 and 17 has the characteristics of the temperature dependence, the resistance value Rpm is changed in accordance with the change of temperature of the sensor element 13 even if the quantity of particulate matter PM accumulated between the detection electrodes 16 and 17 is not changed. However, the microcomputer 51 in the ECU 50 adjusts the power supply to the heater 18 on the basis of the temperature of the sensor element 13 detected in the second state in which a current flows in the temperature detection resistance 34. It is possible for the microcomputer 51 in the ECU 50 to adjust the sensor element 13 in the PM detection sensor 10 at the desired temperature while monitoring the actual temperature of the sensor element 13. This makes it possible to detect the quantity of particulate matter PM accumulated in the sensor element 13 in the PM detection sensor 10 with high accuracy.

Because the quantity of particulate matter PM accumulated between the detection electrodes 16 and 17 which is detected during the first state is adjusted on the basis of the temperature of the sensor element 13 detected in the second state, that is, because the detected quantity of accumulated particulate matter PM is adjusted on the basis of the resistance value Rpm between the detection electrodes 16 and 17, it is possible to execute the temperature adjustment in consideration with the temperature dependence of the resistance value Rpm corresponding to the detected quantity of accumulated particulate matter PM. As a result, this makes it possible to further increase the accuracy of detecting the quantity of particulate matter PM accumulated in the sensor element 13 of the PM detection sensor 10.

OTHER MODIFICATIONS

The present invention is not limited by the embodiment previously described. It is possible for the present invention to have the following modifications.

In the embodiment previously described, the first state and the second state are switched by selecting one of the supply of the DC voltage signal and the supply of the AC voltage signal to the sensor element 13 by using the capacitor 35 connected in series to the temperature detection resistance 34. In the first state, no current flows in the temperature detection resistance 34. On the other hand, in the second state, a current flows in the temperature detection resistance 34.

However, the present invention is not limited by this structure. For example, it is possible to use a switching member, instead of using the capacitor 35, connected in series to the temperature detection resistance 34. The switching member is open in the first state, and the switching member is closed in the second state. This modification can make the first state and the second state.

Further, it is possible to detect wire damage of the PM detection sensor 10 on the basis of the PM detection voltage (as the detection value of the resistance Rpm) obtained in the second state. When such wire damage occurs in the PM detection sensor 10, for example, when wire breaking occurs, the PM detection voltage becomes zero (=0) because it is impossible to detect the resistance value Rpm of the PM detection part 14.

In the first state, when no particulate matter PM is accumulated in the sensor element 13, the resistance value between the detection electrodes 16 and 17 becomes infinitive (=∞), and the PM detection voltage becomes zero (=0). Accordingly, it is impossible for the microcomputer 51 in the ECU 50 to specify whether or not the PM detection voltage of zero is caused by no quantity of accumulated particulate matter PM or by wire breaking in the PM detection sensor 10.

On the other hand, in the second state, when the quantity of accumulated particulate matter PM is zero, the resistance value Rpm takes infinitive (=∞) and the PM detection voltage does not take zero (≠0) because the resistance component of the temperature detection resistance 34 is detected. Accordingly, the PM detection voltage in the second state becomes the parameter of indicating abnormal state diagnosis. It is therefore possible for the present invention to specify whether or not wire breaking occurs in the PM detection sensor 10.

The period of time of executing the process of detecting the temperature of the sensor element 13 is changeable. For example, during the usual condition, the process of detecting the temperature of the sensor element 13 is executed at the predetermined period of time (for example, every 128 msec). On the other hand, during the transition of the temperature change and the process of eliminating particulate matter PM from the PM detection sensor 10, the process of detecting the temperature of the sensor element 13 is executed at a short period of time (for example, every 64 msec) which is shorter than the usual period of time. This makes it possible to execute the temperature control of the sensor element 13 in the PM detection sensor 10 with high accuracy by the control of supplying electric power to the heater 18.

In the embodiment previously described, the capacitor 35 is placed in the PM detection sensor 10 with which the first state and the second state are switched. In the first state, no current flows in the temperature detection resistance 34. In the second state, current flows in the temperature detection resistance 34. That is, the microcomputer 51 instructs the electric power source device 55, namely, the switch part 55c to select the DC power source part 55a in order for the capacitor 35 to make the first state in order to supply the DC voltage (or a DC signal) to the conductive path on which the temperature detection resistance 34 and the capacitor 35 are placed in series. Further, the microcomputer 51 instructs the switch part 55c to select and supply the AC power source part 55b in order for the capacitor 35 to make the second state in order to supply the AC voltage (or a AC signal) to the conductive path on which the temperature detection resistance 34 and the capacitor 35 are placed in series.

The present invention is not limited by this. For example, it is possible to place the capacitor 35 at an outside position of the exhaust gas pipe EP as long as the outside position is not affected by heat energy of the exhaust gas. For example, it is possible to place the capacitor 35 in a device other than the inside of the PM detection sensor 10.

Figure 8:
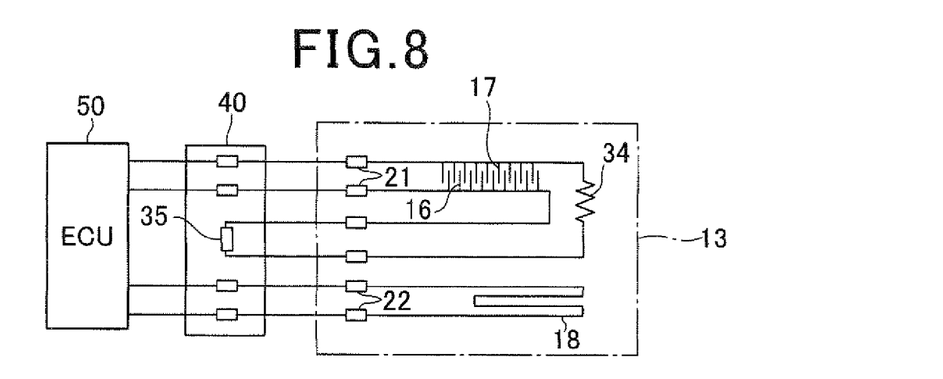
FIG. 8 is a view showing another structure of the PM detection sensor system having the PM detection sensor according to a modification of the embodiment of the present invention.

FIG. 8 is a view showing another structure of the PM detection sensor system having the PM detection sensor 10 according to a modification of the embodiment of the present invention.

As shown in FIG. 8, the capacitor 35 is placed in the inside of the sensor connector 40. This makes it possible to provide a PM detection sensor unit which is comprised of the PM detection sensor 10 and the sensor connector 40. In particular, the temperature detection resistance 34 is formed in the PM detection sensor 10 and the capacitor 35 is formed in the inside of the sensor connector 40.

In the embodiment previously described, the temperature detection resistance 34 and the capacitor 35 make the series circuit at the front end side of the sensor element 13. The present invention is not limited by this structure.

Figure 9:
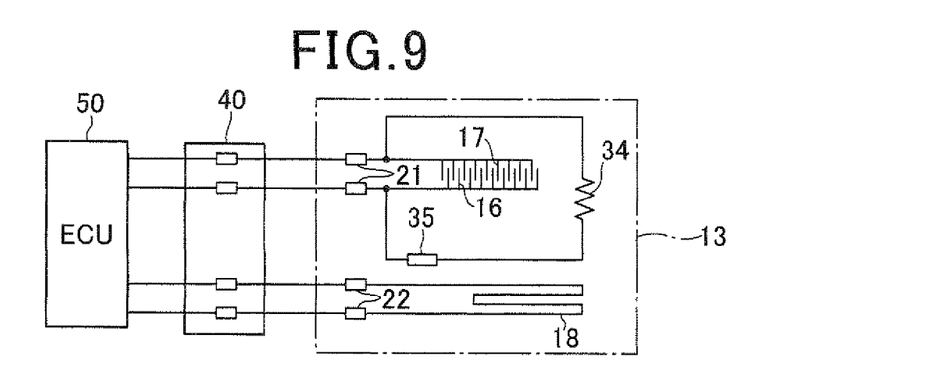
FIG. 9 is a view showing another structure of the PM detection sensor system having the PM detection sensor according to a modification of the embodiment of the present invention.

FIG. 9 is a view showing another structure of the PM detection sensor system having the PM detection sensor 10 according a modification of the embodiment of the present invention.

As shown in FIG. 9, it is possible to connect the series circuit comprised of the temperature detection resistance 34 and the capacitor 35 to the distal end of the detection electrodes 16 and 17 in the sensor element 13.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A particulate matter detection sensor comprising a sensor element capable of detecting particulate matter of conductive characteristics contained in a target detection gas, the sensor element comprising:
   a substrate;
   a pair of detection electrodes formed on the substrate, the detection electrodes facing to each other;
   a temperature detection resistance formed in a conductive path between the pair of the detection electrodes, a temperature of the sensor element being detected on the basis of a resistance value of the temperature detection resistance; and
   a switching means making a first state and second state, in the first state no current flowing through the temperature detection resistance and a quantity of particulate matter accumulated in the sensor element being detected, and in the second state a current flowing through the temperature detection resistance and a temperature of the sensor element being detected during the second state, and a quantity of particulate matter accumulated between the PM detection electrodes being detected on the basis of a change of the resistance value between the detection electrodes caused by the accumulated particulate matters of conductive characteristics;
   wherein the switching means is comprised of a capacitor, the capacitor is connected in series to the temperature detection resistance formed in the conductive path, and the capacitor as the switching means receives one of a direct current signal and an alternating current signal supplied from an electric power source through the pair of the detection electrodes, and the capacitance as the switching means makes the first state when receiving the direct current signal which is supplied from the electric power source to the pair of the detection electrodes, and makes the second state when receiving the alternating current signal which it supplied from the electric power source to the pair of the detection electrodes.

2. The particulate matter detection sensor according to claim 1, wherein the capacitor is placed at a distal end of the sensor element and the temperature detection resistance is placed at a front side of the sensor element when observed along a longitudinal direction of the sensor element.

3. The particulate matter detection sensor according to claim 1, further comprising a heater which generates heat energy when receiving electric power in order to heat the sensor element,
   wherein the heater generates heat energy when receiving electric power supplied from the electric power source under a control by a control means on the basis of the temperature of the sensor element detected in the second state.

4. The particulate matter detection sensor according to claim 1, the quantity of particulate matter accumulated between the pair of the detection electrodes detected in the first state is adjusted on the basis of the temperature of the sensor element detected in the second state.

5. The particulate matter detection sensor according to claim 1, wherein occurrence of wire breaking in the sensor element is detected on the basis of the resistance between the detection electrodes detected in the second state.

6. A particulate matter detection sensor unit comprising:
   the sensor element according to claim 1; and
   a sensor connector connected to the sensor element which wire harness comprising sensor wires connected to the detection electrodes and heater wires connected to the heater.

7. The particulate matter detection sensor unit according to claim 6, wherein the capacitor as the switching means formed in the inside of the sensor connector.

8. A particulate matter detection sensor system comprising:
   the particulate matter detection sensor according to claim 1, the switching means in the particulate matter detection sensor being comprised of a capacitor, the capacitor being connected in series to the temperature detection resistance formed in the conductive path of the pair of the detection electrodes;
   an electric power source capable of supplying one of a direct current signal and an alternating current signal to the pair of the detection electrodes in the particulate matter detection sensor; and
   a control device which instructs the electric power source to supply the direct current signal to the pair of the detection electrodes in order for the capacitor to make the first state, and to supply the alternating current signal to the pair of the detection electrodes in order for the capacitor to make the second state.

9. The particulate matter detection sensor system according to claim 8, wherein the particulate matter detection sensor further comprises a heater which generates heat energy in order to heat the sensor element when receiving electric power, and
   the control device controls the electric power source to supply electric power to the heater in order to generate heat energy on the basis of the temperature of the sensor element detected in the second state.

10. The particulate matter detection sensor system according to claim 8, wherein the control device adjusts the detected quantity value regarding the quantity of particulate matter accumulated between the pair of the detection electrodes detected in the first state on the basis of the temperature of the sensor element detected in the second state.

11. The particulate matter detection sensor according to claim 8, wherein the control device detects occurrence of wire breaking in the sensor element on the basis of the resistance between the detection electrodes detected in the second state.

* * * * *

UNITED STATES PATENT AND TRADEMARK OFFICE
CERTIFICATE OF CORRECTION

PATENT NO. : 8,578,756 B2
APPLICATION NO. : 13/114318
DATED : November 12, 2013
INVENTOR(S) : Suzuki et al.

Page 1 of 1

It is certified that error appears in the above-identified patent and that said Letters Patent is hereby corrected as shown below:

In the Claims

Column 20, Line 20, should read

6. A particulate matter detection sensor unit comprising:
the sensor element according to claim 1; and
a sensor connector connected to the sensor element ~~which~~through a
wire harness comprising sensor wires connected to the
detection electrodes and heater wires connected to the heater.

Column 20, Line 26, should read

7. The particulate matter detection sensor unit according to claim 6, wherein the capacitor as the switching means is formed in the inside of the sensor connector.

Signed and Sealed this
Eighteenth Day of March, 2014

Michelle K. Lee
*Deputy Director of the United States Patent and Trademark Office*